(12) United States Patent
Fojtik

(10) Patent No.: US 10,653,874 B2
(45) Date of Patent: *May 19, 2020

(54) APPARATUS FOR MANUALLY MANIPULATING HOLLOW ORGANS

(71) Applicant: CIRCA Scientific, Inc., Englewood, CO (US)

(72) Inventor: Shawn P. Fojtik, Park City, UT (US)

(73) Assignee: CIRCA Scientific, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/690,041

(22) Filed: Aug. 29, 2017

(65) Prior Publication Data

US 2018/0015268 A1    Jan. 18, 2018

Related U.S. Application Data

(63) Continuation of application No. 12/778,969, filed on May 12, 2010, now Pat. No. 9,744,339.

(51) Int. Cl.
*A61M 29/00* (2006.01)
*A61M 29/02* (2006.01)
(Continued)

(52) U.S. Cl.
CPC ......... *A61M 29/02* (2013.01); *A61B 17/0218* (2013.01); *A61B 18/1492* (2013.01);
(Continued)

(58) Field of Classification Search
CPC .............. A61M 25/09; A61M 25/0041; A61M 2025/09141; A61M 2025/09166;
(Continued)

(56) References Cited

U.S. PATENT DOCUMENTS 2,756,752 A    7/1956 Irving
D237,116 S    10/1975 Ekbladh
(Continued)

FOREIGN PATENT DOCUMENTS

EP    1504725 A1    2/2005
JP    HEI101107307 A    7/1989
(Continued)

OTHER PUBLICATIONS

State Intellectual Property Office of the People's Republic of China, Notification of the First Office Action, CN App. No. 201711418339. 3, dated Sep. 26, 2018.
(Continued)

*Primary Examiner* — Thomas A Giuliani
(74) *Attorney, Agent, or Firm* — Durham Jones & Pinegar, P.C., Intellectual Property Law Group

(57) ABSTRACT

An apparatus for mechanically manipulating hollow organs within the body of a subject, or an organ manipulation apparatus, includes a manipulation section. The manipulation section may include a substantially two-dimensional element, which may have a width that exceeds a distance across a portion of the interior of a hollow organ within which the manipulation section is to be positioned. The manipulation section is configured to manipulate at least a portion of a hollow organ from within, which may modify at least one of a shape, orientation, or location of at least part of the hollow organ. Methods for manipulating hollow organs are also disclosed, as are operating techniques, such as left atrial ablation, in which the shapes, orientations, and/or locations of hollow organs are manipulated to move the hollow organs away from the site of the medical procedure, reducing the potential for damage to the hollow organs.

15 Claims, 4 Drawing Sheets

(51) Int. Cl.

| | | |
|---|---|---|
| *A61B 17/02* | (2006.01) | |
| *A61B 18/14* | (2006.01) | |
| *A61B 90/00* | (2016.01) | |
| A61M 25/09 | (2006.01) | |
| A61B 17/00 | (2006.01) | |
| A61B 17/32 | (2006.01) | |
| A61B 18/00 | (2006.01) | |

(52) U.S. Cl.
CPC .... *A61B 90/04* (2016.02); *A61B 2017/00243* (2013.01); *A61B 2017/00557* (2013.01); *A61B 2017/00867* (2013.01); *A61B 2017/320048* (2013.01); *A61B 2018/00011* (2013.01); *A61B 2018/00357* (2013.01); *A61B 2018/00547* (2013.01); *A61B 2018/00577* (2013.01); *A61B 2018/00797* (2013.01); *A61B 2018/00839* (2013.01); *A61B 2090/0427* (2016.02); *A61B 2090/0481* (2016.02); *A61B 2090/3966* (2016.02); *A61M 2025/09008* (2013.01)

(58) Field of Classification Search
CPC ..... A61M 2025/09008; A61B 18/1492; A61B 17/0218; A61B 90/04; A61B 2017/00867; A61B 2090/0427; A61B 2090/0436
USPC ............. 606/1, 32, 33, 41, 46, 47, 191, 192; 607/96, 98, 99, 101, 115, 116, 124; 600/115, 116, 139, 143, 144, 146, 151
See application file for complete search history.

(56) References Cited

U.S. PATENT DOCUMENTS

| | | | |
|---|---|---|---|
| D282,965 S | 3/1986 | Wellenstam | |
| 5,170,803 A | 12/1992 | Hewson et al. | |
| 5,211,183 A * | 5/1993 | Wilson | A61M 25/0158 600/434 |
| 5,325,848 A | 7/1994 | Adams et al. | |
| 5,382,231 A | 1/1995 | Shlain | |
| 5,391,155 A | 2/1995 | Sachse | |
| 5,536,274 A | 7/1996 | Neuss | |
| 5,673,695 A | 10/1997 | McGee et al. | |
| 5,680,860 A | 10/1997 | Imran | |
| D389,365 S | 1/1998 | Lipson | |
| 5,800,413 A | 9/1998 | Swartz et al. | |
| 5,803,902 A | 9/1998 | Sienkiewicz et al. | |
| 6,015,382 A | 1/2000 | Zwart et al. | |
| 6,080,118 A | 6/2000 | Blythe | |
| 6,080,160 A | 6/2000 | Chen et al. | |
| 6,090,050 A | 7/2000 | Constantinides | |
| 6,106,522 A | 8/2000 | Fleischman et al. | |
| 6,371,928 B1 | 4/2002 | McFann et al. | |
| 6,432,041 B1 | 8/2002 | Taniguchi et al. | |
| 6,589,259 B1 | 7/2003 | Solingen | |
| 6,939,313 B2 | 9/2005 | Saadat et al. | |
| 7,140,766 B2 | 11/2006 | Glukhovsky et al. | |
| 7,293,915 B2 | 11/2007 | Chen | |
| 7,361,180 B2 | 4/2008 | Saadat et al. | |
| 7,621,908 B2 * | 11/2009 | Miller | A61B 17/0218 606/191 |
| D611,601 S | 3/2010 | Tamai et al. | |
| D624,651 S | 9/2010 | Leroy et al. | |
| D624,652 S | 9/2010 | Carus et al. | |
| D625,809 S | 10/2010 | Cuschieri et al. | |
| D625,812 S | 10/2010 | Dapri et al. | |
| D625,813 S | 10/2010 | Dapri et al. | |
| D626,226 S | 10/2010 | Carus et al. | |
| D626,227 S | 10/2010 | Leroy et al. | |
| 7,819,817 B2 | 10/2010 | Rahn | |
| 9,155,476 B2 | 10/2015 | Fojtik | |
| 9,744,339 B2 * | 8/2017 | Fojtik | A61M 29/02 |
| 2002/0133223 A1 | 9/2002 | Vito et al. | |
| 2003/0013985 A1 | 1/2003 | Saadat | |
| 2004/0073132 A1 | 4/2004 | Maahs et al. | |
| 2004/0133273 A1 | 7/2004 | Cox | |
| 2004/0176699 A1 | 9/2004 | Walker et al. | |
| 2004/0186469 A1 | 9/2004 | Vvoloszko et al. | |
| 2004/0215296 A1 | 10/2004 | Ganz et al. | |
| 2005/0033334 A1 | 2/2005 | Santra et al. | |
| 2005/0240116 A1 | 10/2005 | Saadat et al. | |
| 2006/0009715 A1 | 1/2006 | Khairkhahan et al. | |
| 2006/0085054 A1 | 4/2006 | Zikorus et al. | |
| 2006/0106375 A1 | 5/2006 | Werneth et al. | |
| 2006/0116609 A1 | 6/2006 | Kanuka et al. | |
| 2006/0201519 A1 | 9/2006 | Frazier et al. | |
| 2006/0293697 A1 | 12/2006 | Nakao et al. | |
| 2007/0066968 A1 | 3/2007 | Rahn | |
| 2007/0118097 A1 | 5/2007 | Miller | |
| 2007/0118105 A1 | 5/2007 | Miller | |
| 2007/0135733 A1 | 6/2007 | Soukup et al. | |
| 2007/0179378 A1 | 8/2007 | Boese et al. | |
| 2007/0225701 A1 | 9/2007 | O'Sullivan | |
| 2007/0255183 A1 | 11/2007 | Chen | |
| 2008/0033415 A1 * | 2/2008 | Rieker | A61M 25/0147 606/21 |
| 2008/0077126 A1 | 3/2008 | Rashidi | |
| 2008/0177175 A1 | 7/2008 | Mottola et al. | |
| 2008/0215047 A1 | 9/2008 | Calabro et al. | |
| 2008/0234606 A1 | 9/2008 | Itou | |
| 2008/0243112 A1 | 10/2008 | De Neve | |
| 2008/0272776 A1 | 11/2008 | Edelman | |
| 2008/0300590 A1 | 12/2008 | Horne et al. | |
| 2008/0306468 A1 | 12/2008 | Tamai et al. | |
| 2009/0030320 A1 | 1/2009 | Ishihara | |
| 2009/0112248 A1 | 4/2009 | Maloney | |
| 2009/0275956 A1 | 11/2009 | Burnes et al. | |
| 2009/0312602 A1 | 12/2009 | Sakamoto et al. | |
| 2010/0002916 A1 | 1/2010 | Yamaguchi | |
| 2010/0030098 A1 | 2/2010 | Fojtik | |
| 2010/0210944 A1 | 8/2010 | Kondo | |
| 2010/0312223 A1 | 12/2010 | Kozak et al. | |
| 2012/0010524 A1 | 1/2012 | Fojtik et al. | |

FOREIGN PATENT DOCUMENTS

| | | |
|---|---|---|
| JP | 02-203835 A | 8/1990 |
| JP | HEI103-056048 A2 | 8/1990 |
| JP | 2002541905 A | 12/2002 |
| JP | 2005503241 A | 2/2005 |
| JP | 2005-095602 A | 4/2005 |
| JP | 2005270425 A | 10/2005 |
| JP | 2007537784 A | 12/2007 |
| WO | 200062699 A2 | 10/2000 |
| WO | 200243789 A2 | 6/2002 |
| WO | 2005117755 A2 | 12/2005 |
| WO | 2006055286 A2 | 5/2006 |
| WO | 2007001981 A2 | 1/2007 |
| WO | 2009117523 A2 | 9/2009 |
| WO | 2012151584 A1 | 11/2012 |

OTHER PUBLICATIONS

State Intellectual Property Office of the People's Republic of China, Search Report, CN Application No. 201711418339.3, dated Sep. 26, 2018.
Japan Patent Office, Office Action, JP Application No. 2017-217984, dated Aug. 27, 2018.
Merriam-Webster's Collegiate Dictionary 10th ed. Merriam-Webster, Inc. 2001. p. 449.
European Patent Office, "Supplementary European Search Report," in European application No. 09721913.3, May 8, 2013.
European Patent Office, "Supplementary European Search Report," in European application No. 11781308.9, dated Nov. 5, 2014.
Sine wave amplitude, Retrieved from Internet, <URL: http://www.wikipedia.org> on Mar. 24, 2011, May 12, 2008.
Waveforms, Retrieved from Internet, <URL: http://www.wikipedia.org> on Mar. 24, 2011, Oct. 23, 2006.
International Searching Authority, Korean Intellectual Property Office, "International Search Report and Written Opinion," PCT application No. PCT/US2009/037571, dated Nov. 2, 2009.

(56) References Cited

OTHER PUBLICATIONS

International Searching Authority, United States Patent and Trademark Office, "International Search Report and Nritten Opinion," PCT application No. PCT/US2011/036330, dated Aug. 16, 2011.
International Searching Authority, United States Patent and Trademark Office, "International Search Report and Written Opinion," PCT application No. PCT/US2012/036814, dated Aug. 14, 2012.
Japanese Patent Office, "Final Notification of Reasons for Rejection," Japanese patent application No. 9 2013-510314, dated Dec. 19, 2014.
Hartwell, R.M., "An Improved Sine to Square Wave Convertor for Rife/Bare Systems," Retrieved from Internet, <URL: http://www.w5jgv.com> on on Mar. 24, 2011, May 24, 2001.
Sine wave, Retrieved from Internet ,<URL: http:// www.wikipedia.org> on Dec. 14, 2010, Nov. 7, 2006.
State Intellectual Property Office of the People's Republic of China, "First Office Action," Chinese application No. 201180031268.6, Mar. 5, 2014.
State Intellectual Property Office of the People's Republic of China, "Second Office Action," Chinese application No. 201180031268.6, dated Oct. 20, 2014.
State Intellectual Property Office of the People's Republic of China, "Third Office Action," Chinese application No. 201180031268.6, dated Apr. 9, 2015.
State Intellectual Property Office of the People's Republic of China, "Fourth Office Action," Chinese application No. 201180031268.6, dated Oct. 8, 2015.
State Intellectual Property Office of the People's Republic of China, "Rejection Decision," Chinese application No. 201180031268.6, dated Apr. 8, 2016.
State Intellectual Property Office of the People's Republic of China, "Second Office Action," Chinese application No. 2017114183393, May 10, 2019.
Japanese Patent Office, "Reasons for Rejection," Japanese patent application No. 2013-510314, dated Dec. 3, 2013.

* cited by examiner

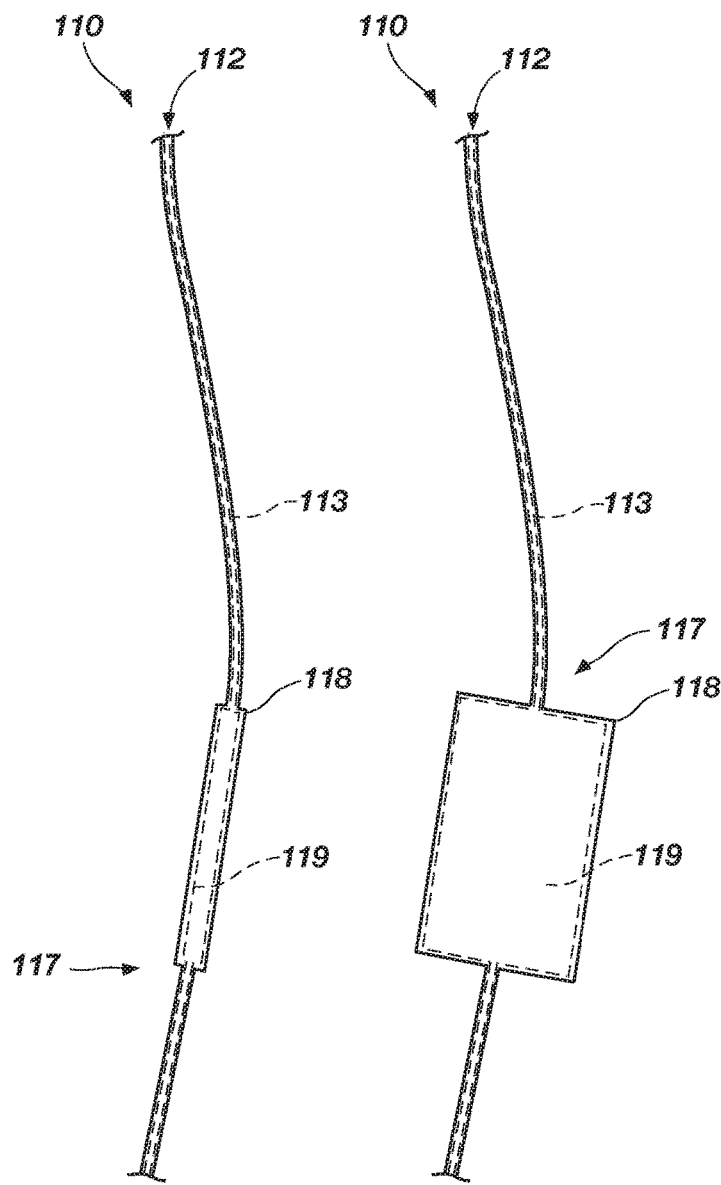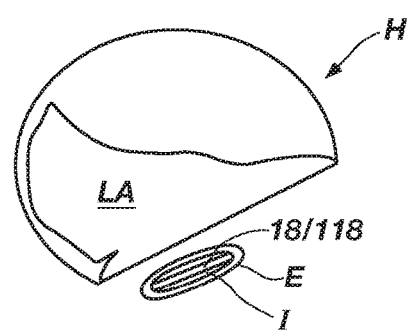
FIG. 7　　FIG. 8　　FIG. 9

APPARATUS FOR MANUALLY MANIPULATING HOLLOW ORGANS

CROSS-REFERENCE TO RELATED APPLICATION

This application is a continuation of U.S. patent application Ser. No. 12/778,969, filed on May 12, 2010 and titled APPARATUS FOR MANUALLY MANIPULATING HOLLOW ORGANS ("the '969 application"), now U.S. Pat. No. 9,744,339, issued Aug. 29, 2017. The entire disclosure of the '969 application is hereby incorporated herein.

TECHNICAL FIELD

The present invention relates generally to apparatuses for mechanically manipulating hollow organs within the body of a subject. More specifically, the present invention relates to apparatuses that are useful for causing at least portions of hollow organs to move away from locations where medical procedures that might otherwise damage the hollow organs are performed. The present invention also relates to surgical procedures in which a hollow organ mechanically manipulated, including, but not limited to, procedures in which a hollow organ is moved at least partially away from the site of a medical procedure (e.g., a surgical procedure, such as a thermal procedure or an electrical procedure, etc.).

BACKGROUND OF RELATED ART

A variety of techniques have been developed in which tissues or organs in a patient's body are heated or cooled. Tissues may be heated by a variety of techniques, including high frequency ultrasound, radiofrequency (RF) treatments, laser treatments, use of infrared radiation, and by direct application of thermal energy. Cooling is often effected cryogenically. Techniques that heat and cool tissues may be collectively referred to as "thermal techniques."

Thermal techniques are useful for diagnosing a variety of disease states and for treating a variety of disease states. More specifically, thermal techniques may be used to diagnose and/or treat cancerous tissues, to destroy diseased tissues, to congeal blood, and to perform a variety of other diagnostic and surgical procedures. Examples of organs that may be subjected to thermal techniques include the heart, the lungs, gastrointestinal organs, the liver, the pancreas, urological organs, prostates, reproductive organs, and skin.

The degree of heating or cooling that is required to optimize the efficiency of some thermal techniques may adversely affect tissues or organs that are adjacent to a treated tissue or organ. For example, a great deal of heat is generated when left atrial ablation techniques are used to treat atrial fibrillation in human subjects. In addition to heating and treating the diseased tissue in the heart H, the esophagus E, which is adjacent to the left atrium LA of the heart H, as shown in FIG. 1, may also be heated. As FIG. 1 illustrates, a human esophagus E typically has a narrow oval shape that resembles a pancake, with a large portion of the outer surface of the esophagus E located next to or in contact with the left atrium LA, although the size, shape, and/or position of the esophagus E may vary. In an average human adult, about 58 mm of the length and the majority of the front side of a 14 mm diameter esophagus E is located in proximity to or contacts the left atrium LA. As a consequence of this intimate arrangement between the esophagus E and the left atrium LA, the heat generated during left atrial ablation may damage the esophagus E and may, in some cases, create an esophageal fistula. Unfortunately, the complications that arise from esophageal fistula may not present themselves until weeks after the procedure and, in many cases, at too late a time to treat and/or cure the sometimes fatal damage that has been done.

In recognition of the potentially dire consequences of overheating the esophagus E during left atrial ablation, some physicians have started using catheters with temperature sensors to monitor the temperature within the subject's esophagus E. Typically, a catheter with a size of 9 French (about 3 mm diameter) to about 18 French (about 64 mm diameter) is used in conjunction with a conventional temperature sensor (e.g., an esophageal stethoscope available from Smiths Medical of Hythe, Kent, United Kingdom). If the sensed temperature reaches a predetermined level, the physician may discontinue the left atrial ablation momentarily to allow the esophagus E to cool.

In a further effort to reduce the likelihood of esophageal fistula during left atrial ablation procedures, a variety of different types of inflatable devices have been developed. Some inflatable devices are configured to cool the esophagus E during left atrial ablation. Other inflatable devices are configured to ensure contact between one or more temperature sensors and the interior surface of the front of the esophageal wall. Despite assertions to the contrary, since the esophagus E is confined between the left atrium LA of the relatively rigid heart H and the even more rigid vertebral column VC (see FIG. 1), the inflation of a device within the esophagus E merely distends the esophagus E or pushes the esophagus E closer to, or into more intimate contact with, the left atrium LA. The obvious result of such distension is an increase in the likelihood that a left atrial ablation procedure will cause an esophageal fistula. In addition, use of an inflatable device will undesirably prevent a subject from swallowing during the typically lengthy (two to four hour) procedure, which may unnecessarily require that the subject be placed under general anesthesia, which increases the risks associated with the procedure.

SUMMARY

The present invention includes various embodiments of apparatuses for mechanically manipulating hollow organs. Such apparatuses are also referred to herein as "organ manipulation apparatuses."

An organ manipulation apparatus of the present invention may comprise an elongate element configured for insertion into the interior of a hollow organ. Such an apparatus may include a manipulation section for temporarily altering at least one characteristic (e.g., shape, orientation, position, etc.) of at least a portion of the hollow organ within which the manipulation section is positioned.

In a specific embodiment, the manipulation section of an organ manipulation apparatus of the present invention may be configured to flatten, or "tent," a hollow organ. More specifically, a manipulation section of an organ manipulation apparatus may have a width that exceeds a distance across the interior of the hollow organ within which the manipulation section is configured to be placed.

The manipulation section may, in some embodiments, comprise a substantially two-dimensional structure, having a thickness that does not substantially exceed (e.g., is no more than about twice the thickness of other portions of the organ manipulation apparatus, etc.). The arrangement of such an embodiment of manipulation section is referred to as a "substantially two-dimensional arrangement" to account for the thicknesses of the elongate element, as well as for any slight deviations of the elongate element from a desired plane for the two-dimensional arrangement.

In other embodiments, the manipulation section may have a more three-dimensional configuration.

An organ manipulation apparatus of the present invention may comprise part of a system for effecting an operating technique. By way of example, in addition to an organ manipulation apparatus, such a system may include an apparatus used in a medical procedure, such as a device that applies energy, heat, or cold to a desired tissue (e.g., a radiofrequency catheter, etc.).

In another aspect, the present invention includes a variety of embodiments of methods for manipulating hollow organs. A hollow organ may be manipulated in accordance with teachings of the present invention as or after a manipulation section of an organ manipulation apparatus is introduced into an interior of a hollow organ. In some embodiments, the manipulation section of an organ manipulation apparatus may have a substantially one-dimensional configuration when introduced into the interior of a hollow organ, then assume a substantially two-dimensional configuration or a three-dimensional configuration once the manipulation section has been positioned within the interior of the hollow organ. Alternatively, a manipulation section of an organ manipulation apparatus already having a substantially two-dimensional configuration or even a three-dimensional configuration may be introduced into the interior of the hollow organ.

The present invention also includes operating techniques in which hollow organs are manipulated as medical procedures are conducted. An operating technique of the present invention includes manipulating at least a portion of a hollow organ within the body of a subject. The hollow organ may be manipulated by introducing at least a manipulation section of an organ manipulation apparatus into the interior of the hollow organ or after the manipulation section has been introduced into the interior of the hollow organ. Manipulation may include, but is not limited to, alteration of the shape of all or part (e.g., the portion in which the manipulation section resides, etc.) of the hollow organ (e.g., flattening, or "tenting," of the hollow organ, etc.), a change in the orientation of all or part of the hollow organ, movement of at least a portion of the hollow organ, or the like. In some embodiments of an operating technique that incorporates teachings of the present invention, manipulation of the hollow organ moves the hollow organ away from a site at which a medical procedure is to be conducted.

In addition to manipulating the hollow organ, an operating technique of the present invention includes conducting a medical procedure at or near a site from which a hollow organ, or at least a portion of a hollow organ, has been moved. In some embodiments movement of a hollow organ away from the site of the medical procedure may reduce or eliminate damage to the hollow organ during the medical procedure. Examples of medical procedures that may damage adjacent tissues include, but are by no means limited to, procedures in which an extreme temperature (e.g. heat or cold), electricity, or radiation is applied to or generated at a site that is naturally adjacent to another organ within the body of the subject.

Other aspects, as well as various features and advantages of different aspects, of the present invention will become apparent to those of ordinary skill in the art through consideration of the ensuing description, the accompanying drawings, and the appended claims.

BRIEF DESCRIPTION OF THE DRAWINGS

In the drawings:

FIGS. 7 and 8 depict an embodiment of organ manipulation apparatus that includes a manipulation section with a balloon, which is in a deflated, substantially one-dimensional configuration in FIG. 7 and in an inflated, substantially two-dimensional configuration in FIG. 8;

FIG. 9 illustrates manipulation of a hollow organ by an embodiment of organ manipulation apparatus, as well as use of the embodiment of organ manipulation apparatus in conjunction with a procedure in which a medical procedure is employed.

DETAILED DESCRIPTION

Figure 2:
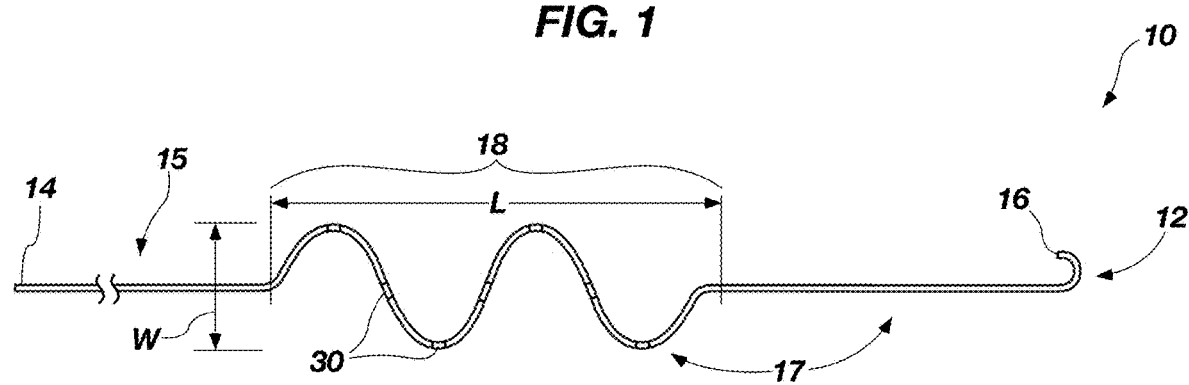
FIG. 2 depicts an embodiment of an organ manipulation apparatus with an elongate member that includes a manipulation section with a substantially two-dimensional arrangement.

As shown in FIG. 2, one embodiment of an organ manipulation apparatus 10 of the present invention comprises an elongate element 12 with a proximal end 14 and a distal end 16. The proximal end 14 is configured to be manipulated by a user, such as a doctor or other healthcare professional, while the distal end 16 is configured for insertion into the body, and into an interior of a hollow organ within the body, of a subject.

An organ manipulation apparatus 10 may comprise, consist essentially of, or even consist of the elongate element 12.

In some embodiments, the elongate element 12, or a portion thereof, may comprise a suitable medical grade plastic. In embodiments where all or part of the elongate element 12 is formed from a plastic, the plastic may comprise a polyester, a polyurethane, a latex, polyvinyl chloride, and the polyether block amide marketed as PEBAX®.

In other embodiments, the elongate element 12, or at least a portion thereof, may include a wire. The wire of such an embodiment may include an elongate solid filament, a wound filament, a combination of solid and wound sections, or any other suitable configuration. In embodiments where a wire is used as all or part of the elongate element 12, the wire may be formed from any suitable medical grade metal or metal alloy. Metals and/or metal alloys that may be used to form all or part of elongate element 12 include, but are not limited to, stainless steel, shape memory alloys such as the nickel-titanium alloy referred to as "nitinol" (for nickel titanium naval ordinance laboratory), nickel-titanium, platinum, cobalt-chromium, and the cobalt-based alloy available under the trade name ELIGLOY®.

In a specific embodiment where all or part of the elongate element 12 comprises a wire, the wire has a diameter of about 0.035 inch to about 0.038 inch. An elongate element 12 or portion of an elongate element 12 that is formed from a metal or metal alloy may, in some embodiments, be coated with a softer polymer to prevent damage to the tissues and organs of the body of a subject into which the organ manipulation apparatus 10 is introduced. In a more specific embodiment, the wire may include a core and another filament wound around the distal-most portion of the core, with a remainder of the distal portion 17 of the wire consisting of the solid filament that forms the core. The core may be formed from steel, nitinol, another nickel-titanium alloy, or any other suitable material. The wire wrap that forms the coil may also be formed from any suitable material, including, but not limited to, steel, tungsten, platinum, or the like.

The entire elongate element 12 may be formed from the same material, or have a hybrid construction.

An organ manipulation apparatus 10 may include a radiopaque material. The inclusion of a radiopaque material may be considered to be non-essential to the function of the organ manipulation apparatus 10. Examples of suitable radiopaque materials include, but are not limited to, gold, iridium, platinum, tungsten, and barium, which is useful with polymers. In some embodiments, all or part of the elongate element 12 may comprise a radiopaque material. In other embodiments, one or more radiopaque elements 30 may be provided along one or more parts of the elongate element 12. Without limiting the scope of the present invention, radiopaque elements 30 may include radiopaque material infused into a material of the elongate element 12 (e.g., barium infused into a polymer), a coating or plating of radiopaque material on one or more portions of the elongate element 12, separate elements (e.g., swage bands, etc.) that have been applied to the elongate element 12, or disposed internally (e.g., as a core, etc.) within all or part of the elongate element 12. The radiopaque material may enable a user, such as a physician or other healthcare provider, to visualize the position and orientation of a desired portion of the elongate element 12 within the interior of a hollow organ.

In some embodiments, a portion of the elongate element 12 of an organ manipulation apparatus 10 may carry electrodes (e.g., for electrocardiogram monitoring, etc.), temperature sensors, or combinations of electrodes and temperature sensors.

In the depicted embodiment of organ manipulation apparatus 10, a proximal portion 15 of the elongate element 12, adjacent to the proximal end 14 of the elongate element 12, is substantially linear, or substantially one-dimensional.

A distal portion 17 of the elongate element 12, which includes a manipulation section 18, is adjacent to the distal end 16 of the elongate element 12 of the organ manipulation apparatus 10. The manipulation section 18 may have a substantially two-dimensional configuration, or even a three-dimensional configuration, as opposed to the substantially one-dimensional configuration of the proximal portion 15 of the elongate element 12 of the organ manipulation apparatus 10. A width W of the manipulation section 18 may exceed a distance across a portion of the interior of the hollow organ within which the distal portion 17 of the elongate element 12 of the organ manipulation apparatus 10 is configured to be positioned, which may cause the hollow organ to at least partially flatten, or tent, as the manipulation section 18 is positioned within that portion of the interior of the hollow organ.

In a specific embodiment, the manipulation section 18 of a distal portion 17 of an elongate element 12 of an organ manipulation apparatus 10 of the present invention has a width W of about 15 mm to about 20 mm. In such an embodiment, a length L of the manipulation section 18, or of a section of the distal portion 17 that is wider than the thickness of the elongate element 12, may be about 70 mm.

The manipulation sections 18 of the distal portions 17 of the elongate elements 12 of some embodiments of organ manipulation apparatuses 10, such as that depicted by FIG. 2, may be configured as waves. An amplitude W of the wave exceeds a distance across at least a portion of the interior of a hollow organ within which the manipulation section 18 is configured to be positioned. While FIG. 2 depicts a manipulation section 18 that has the shape of a sinusoidal waveform, the manipulation section 18 of the distal portion 17 of the elongate element 12 of an organ manipulation apparatus 10 of the present invention may be configured as any other suitable type or shape of waveform. Non-limiting examples include other regular waveforms, random waveforms with varying amplitudes and/or frequencies, damped or distorted waveforms, and the like. Manipulation sections 18 with other configurations, such as loops, spirals, laterally offset elements, and the like, are also within the scope of the present invention.

The configurations (e.g., shapes, dimensions, etc.) of the manipulation sections 18 of the distal portions 17 of the elongate elements 12 of various embodiments of organ manipulation apparatuses 10 that incorporate teachings of the present invention may be preformed, or defined, during manufacture of the organ manipulation apparatus 10. Alternatively, the manipulation sections 18 of some embodiments may be formed to (e.g., bent into, etc.) a desired configuration by a user.

The distal portion 17 of the elongate element 12 may have sufficient rigidity, while in place within the interior of the hollow organ, to retain its shape enough to enable manipulation of the hollow organ (e.g., its shape, orientation, position, etc.). In some embodiments, the manipulation section 18 of the distal portion 17 may be somewhat lacking in flexibility, enabling it to manipulate the hollow organ, but have a configuration (e.g., shape, dimensions, etc.) that enables the distal portion 17 to be inserted into the interior of a hollow organ within the body of a subject without damaging the hollow organ or any of its tissues.

In other embodiments, the distal portion 17 of the elongate element 12 of an organ manipulation apparatus 10 of the present invention may be sufficiently flexible to facilitate its introduction into the body of a subject, and into the interior of a hollow organ within the subject's body, without damaging the hollow organ or any of its tissues.

Figures 3, 4, 5, 6:
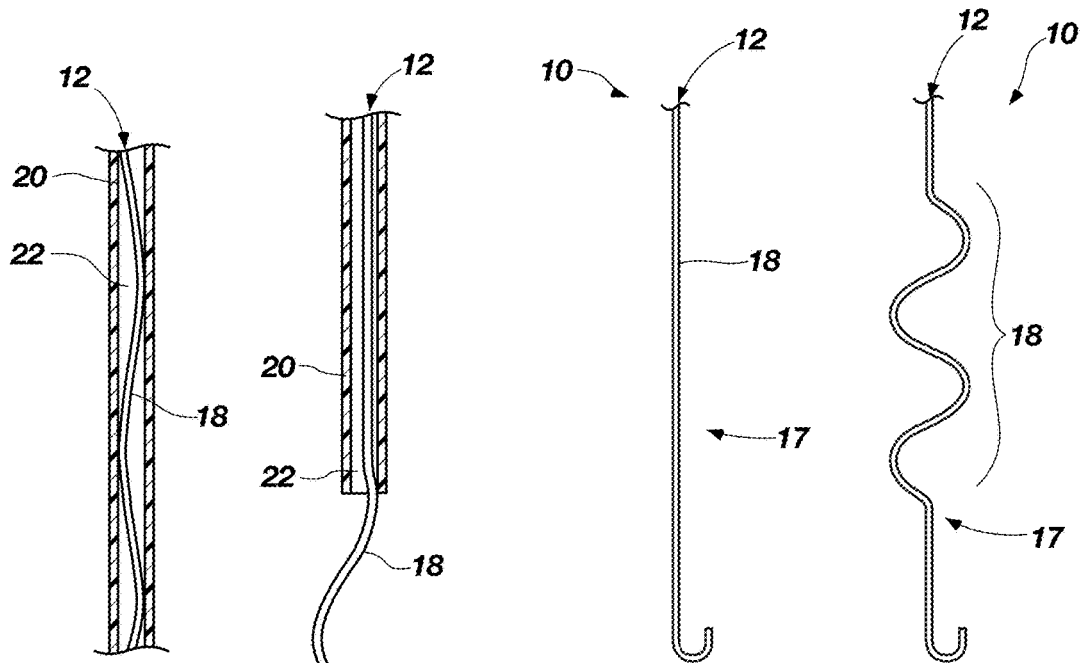
FIG. 3 illustrates the embodiment of organ manipulation apparatus, such as that shown in FIG. 2, in a substantially linear, or substantially one-dimensional, configuration in a stressed state within a lumen of a catheter having a substantially linear, or substantially one-dimensional, configuration.
FIG. 4 depicts relaxation of a segment of the embodiment of organ manipulation apparatus shown in FIG. 2 to its substantially two-dimensional arrangement upon exiting a distal end of the catheter of FIG. 3.
FIG. 5 shows an embodiment of organ manipulation apparatus that is substantially linear, or substantially one-dimensional, when exposed to certain conditions.
FIG. 6 illustrates the embodiment of organ manipulation apparatus of FIG. 5, which has assumed a substantially two-dimensional configuration or a three-dimensional configuration upon exposure to at least one condition within the interior of a hollow organ.

Specifically, such an organ manipulation apparatus 10 may include an elongate element 12 with a distal portion 17 that includes a manipulation section 18 formed from a material that may take on a substantially linear, or one-dimensional, configuration when stressed. FIG. 3 illustrates an example of the manner in which the manipulation section 18 may be stressed into a substantially linear, or one-dimensional, configuration: by confining the manipulation section 18 within the lumen 22 of a suitable introduction element 20 (e.g., a catheter, another tube, etc.). By confining the manipulation section 18 to a substantially linear, or one-dimensional, configuration, the introduction element 20 may facilitate introduction of the manipulation section 18 to a desired location within the interior of a hollow organ. Once the manipulation section 18 has reached the desired location, the introduction element 20 may be removed from the manipulation section 18 (e.g., by pulling the introduction element 20 proximally from the elongate element 12, etc.), as shown in FIG. 4. When removed from the lumen 22 of the introduction element 20, the manipulation section 18 may return to its relaxed state, in which the manipulation section 18 has a substantially two-dimensional configuration, or even a three-dimensional configuration.

As an alternative, the manipulation section 18 of the distal portion 17 of the elongate element 12 of an organ manipulation apparatus 10 of the present invention may initially have a substantially linear, or one-dimensional, configuration when introduced into the body and into the interior of a hollow organ of a subject, as shown in FIG. 5, but may assume a desired configuration upon residing with the interior of the hollow organ, as shown in FIG. 6. For example, the manipulation section 18 may comprise a material (e.g., a nickel titanium alloy, or nitinol, etc.) that is somewhat flexible or selectively flexible under certain conditions (e.g., depending upon its temperature, when exposed to a temperature cooler than body temperature, etc.), and rigid (e.g., has shape memory, etc.) under other conditions (e.g., at body temperature, etc.).

Turning now to FIGS. 7 and 8, another embodiment of organ manipulation apparatus 110 of the present invention is shown. Specifically, organ manipulation apparatus 110 includes an elongate element 112 having a tubular configuration and, thus, including a lumen 113. A manipulation section of the organ manipulation apparatus 110, which comprises a balloon 118 that includes an interior 119 in communication with the lumen 113 of the elongate element 112, is located at a distal portion 117 of the elongate element 112.

The balloon 118 is expandable from a substantially one-dimensional configuration to a substantially two-dimensional configuration. In various embodiments, the balloon 118 may comprise a thinner or more flexible material than the elongate element 112, enabling the balloon 118 to selectively expand from the one-dimensional configuration to the substantially two-dimensional configuration while the elongate element 112 resists expansion.

In the substantially one-dimensional configuration, which is illustrated by FIG. 7, the thickness and width of the balloon 118 are substantially the same as (e.g., no more than about twice, three times, etc.) the corresponding dimensions of adjacent portions of the elongate element 112.

In the substantially two-dimensional configuration, which is depicted by FIG. 8, the width of the balloon 118 may exceed the distance across at least a portion of the interior of an organ in which the balloon 118 is configured to be placed, while the thickness of the balloon 118 is substantially the same as (e.g., no more than about twice, etc.) the thicknesses (e.g., diameters, etc.) of portions of the elongate element 112 that are adjacent to the balloon 118.

In an example of use, the balloon 118 of the organ manipulation apparatus 110 may be introduced into the interior of a hollow organ while in its substantially one-dimensional configuration (FIG. 7), then expanded to its substantially two-dimensional configuration when positioned at a desired location within the interior of the hollow organ. Without limiting the scope of the present invention, the balloon 118 may be expanded by introducing a pressurized fluid (e.g., air, a gas or mixture of gases, a liquid, etc.) into the lumen 113 of the elongate element 112 and into the interior 119 of the balloon 118. As the balloon 118 expands, it may flatten or otherwise manipulate the hollow organ within which it is disposed, changing one or more of the shape, orientation, or location of at least a portion of the hollow organ.

Figure 1:
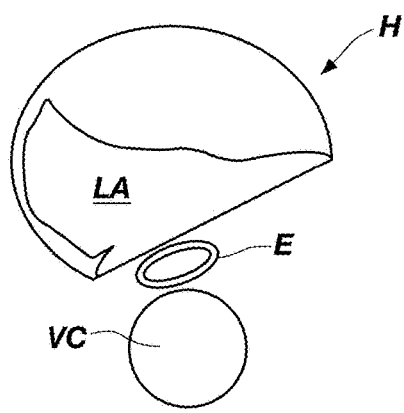
FIG. 1 is a cross-sectional representation of a portion of a human body illustrating the relationship between the esophagus and the heart.

FIG. 9 depicts an embodiment of manipulation of a hollow organ in accordance with teachings of the present invention. Specifically, FIG. 9 shows a manipulation section 18/118 of an organ manipulation apparatus 10/110 (FIGS. 2 and 8) within the interior I of a hollow organ, such as an esophagus E. The manipulation section 18/118 (FIGS. 2-8) partially flattens the esophagus E, changing one or more of the shape, orientation, and position of esophagus E relative to the shape, orientation, and/or position depicted by FIG. 1. The manipulation section 18/118 may be oriented within the interior I of the esophagus E by manipulating the proximal portion 15 (FIG. 2) of the elongate element 12, 112 (FIGS. 2 and 8), such as by pushing, pulling, or twisting the proximal portion 15. When properly oriented or positioned within the interior I of esophagus E, such as in the orientation depicted by FIG. 9, the manipulation section 18/118 of the organ manipulation apparatus 10/110 may move at least a portion of the esophagus E away from the left atrium LA of the heart H.

In some embodiments, including those where at least a portion of the manipulation section 18/118 comprises or includes a radiopaque material, the position or orientation of the manipulation section 18/118 within a portion of the interior of the hollow organ may be visualized with the assistance of a suitable imaging technique (e.g., x-ray, etc.). Visualization of the position or orientation of the manipulation section 18/118 within the interior I of the esophagus E may optimize movement of a desired portion of the esophagus E away from a site, such as the left atrium LA of the heart H, where a medical procedure, such as left atrial ablation, is to be performed.

Both an x-plane (e.g., a section through the diameter of the esophagus E, such as the view illustrated by FIG. 9, etc.) and a y-plane (e.g., a section along the length of the esophagus E, etc.) may be visualized during a medical procedure, such as left atrial ablation. These images may be useful for identifying how a hollow organ has been manipulated, as well as the degree to which it has been manipulated.

When a manipulation section 18/118 is visualized within the interior of a hollow organ (e.g., interior I of the esophagus E, etc.), it may also provide a point of reference, enabling a user to identify dimensions of features within the body of a subject, including features that are visible in both an x-plane, relative to a width of the manipulation section 18/118, and a y-plane, relative to a length of the manipulation section 18/118.

In addition, when the manipulation section 18/118 has a width that exceeds a relaxed distance across a portion of the interior of a hollow organ, the manipulation section 18/118 defines a stressed distance across that portion of the interior of the hollow organ. Thus, visualization of the manipulation section 18/118 may reveal the precise location of at least a portion of the hollow organ itself (which may not otherwise be visible).

Since the manipulation section 18/118 is solid, it may enable consistent imaging of a hollow organ, such as esophagus E, over time. Unlike liquid contrast media, such as barium, manipulation section 18/118 does not flow, and movement of the hollow organ (e.g., peristalsis by the esophagus E, etc.) does not have a significant effect on the shape or location of the manipulation section 18/118. Moreover, use of the manipulation section 18/118 to visualize the esophagus E does not present the risk of aspiration pneumonia that might occur if a liquid contrast medium, such as barium, flows retrograde out of the esophagus E and is aspirated into the lungs of a laying subject.

Figure 10:
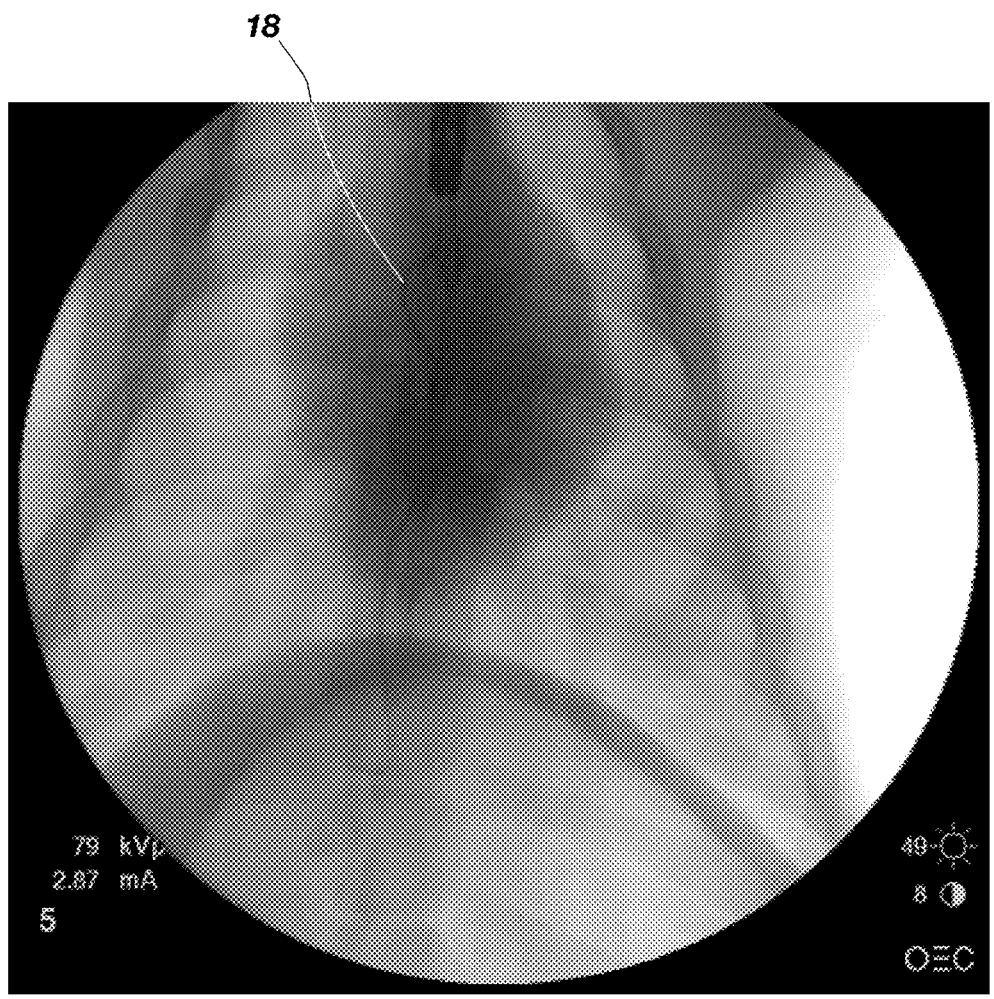
FIGS. 10 and 11 are x-rays showing an embodiment of an organ manipulation apparatus within an esophagus.
Figure 11:
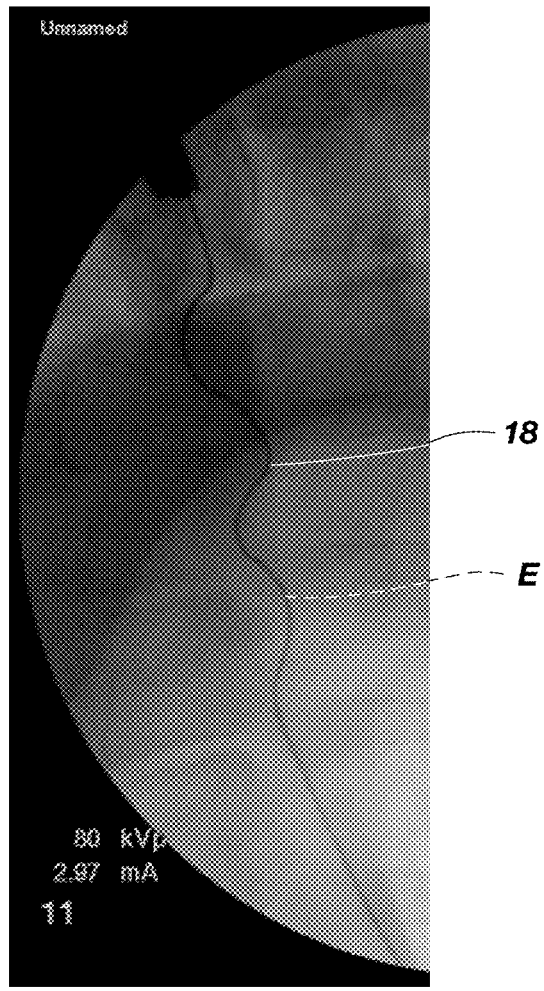

FIGS. 10 and 11 are x-ray images of the y-plane, showing a manipulation section 18 of an organ manipulation apparatus 10/110 (FIGS. 2-6/FIGS. 7 and 8) within an esophagus E. Of course, other organs may visualized in a similar manner when other embodiments of operating techniques that incorporate teachings of the present invention are employed. As the x-ray images of FIGS. 10 and 11 illustrate, an organ manipulation apparatus 10/110 with radiopaque features may be used to visualize a hollow organ while also allowing for viewing of another organ behind the visualized hollow organ (e.g., the heart H and its left atrium LA, etc.).

With the manipulation section 18 (or 118—FIG. 8) of the organ manipulation apparatus 10 (or 110—FIG. 8) properly positioned within the interior I of the esophagus E, a left atrial ablation procedure may be effected with reduced risk of heating and damaging the esophagus E. During a left atrial ablation procedure, an interior surface of a front portion of a subject's esophageal wall located adjacent to the left atrium LA of the subject's heart H may be moved away from the left atrium LA.

The risk of heating and damaging the esophagus E may be further minimized by introducing a cooling fluid (e.g., cooled water, etc.) into the interior I of the esophagus E during the left atrial ablation procedure. With returned reference to FIGS. 2 and 8, In a specific embodiment, the cooling fluid may drip or flow along the elongate element 12/112 of the organ manipulation apparatus 10/110, and over surfaces of the manipulation section 18/118 of the organ manipulation apparatus 10/110. In other embodiments, cooling fluid may flow down and over interior I surfaces of the esophagus E. In still other embodiments, the organ manipulation apparatus 10/110 may be disposed within the lumen of a flexible catheter, and cooling fluid infused into the lumen of the flexible catheter during a left atrial ablation procedure.

Other embodiments of operating techniques are also within the scope of the present invention, including, without limitation, manipulating the trachea during ablation of the pulmonary vein; manipulating the ureters, urethra, and/or colon during thermal treatment of the prostate; manipulation (e.g., flattening, etc.) a portion of the duodenum of the small intestine during thermal treatment of the liver (e.g., to treat hepatic carcinoma, etc.); and manipulation of the gall bladder, cystic duct, bile duct, and/or stomach during thermal treatment of the liver or pancreas.

Although the foregoing description contains many specifics, these should not be construed as limiting the scope of the invention or of any of the appended claims, but merely as providing information pertinent to some specific embodiments that may fall within the scopes of the invention and the appended claims. Other embodiments of the invention may also be devised which lie within the scopes of the invention and the appended claims. Features from different embodiments may be employed in combination. The scope of the invention is, therefore, indicated and limited only by the appended claims and their legal equivalents. All additions, deletions, and modifications to the invention, as disclosed herein, that fall within the meaning and scopes of the claims are to be embraced thereby.

What is claimed:

1. An elongate element of an apparatus for manipulating an esophagus, the elongate element consisting of:
   a distal end;
   a proximal end opposite from the distal end;
   a proximal portion adjacent to the proximal end, the proximal portion being substantially linear or substantially curvilinear; and
   a distal portion adjacent to the distal end, a manipulation section of the distal portion having a substantially two-dimensional configuration defined by a plurality of deviations extending laterally beyond a linear or curvilinear path of the elongate element, the plurality of deviations including at least one deviation extending laterally beyond a first side of the linear or curvilinear path of the elongate element and at least one second deviation extending laterally beyond a second side of the linear or curvilinear path of the elongate element, the substantially two-dimensional configuration having a width of more than 14 mm and a rigidity sufficient to move the esophagus and/or flatten the esophagus.

2. The elongate element of claim 1, wherein the elongate element has a substantially solid structure.

3. The elongate element of claim 1, wherein the elongate element is radiopaque.

4. The elongate element of claim 1, wherein the elongate element is a wire.

5. The elongate element of claim 1, wherein the elongate element has a diameter of about 0.035 inch to about 0.038 inch.

6. The elongate element of claim 1, wherein the manipulation section is made of a shape memory alloy.

7. The elongate element of claim 1, wherein the plurality of deviations impart the manipulation section with a shape of a waveform.

8. The elongate element of claim 1, wherein the plurality of deviations includes a series of curved deviations extending laterally beyond opposite sides of the linear or curvilinear path of the elongate element.

9. The elongate element of claim 8, wherein the plurality of deviations includes at least two curved deviations extending laterally beyond the first side of the linear or curvilinear path of the elongate element.

10. The elongate element of claim 1, wherein the width of the manipulation section is about 15 mm to about 20 mm.

11. An elongate element of an apparatus for manipulating an esophagus,
    the elongate element consisting of:
    a distal end;
    a proximal end opposite from the distal end;
    a proximal portion adjacent to the proximal end, the proximal portion being substantially linear or substantially curvilinear; and
    a distal portion adjacent to the distal end, a manipulation section of the distal portion:
    defined by a plurality of deviations extending laterally beyond opposite sides of a substantially linear path or a substantially curvilinear path of the proximal portion of the elongate element, the plurality of deviations rendering the manipulation section substantially two-dimensional;
    having a width of greater than 14 mm; and having a rigidity sufficient to move the esophagus and/or flatten the esophagus.

12. The elongate element of claim 11, wherein the elongate element is a wire.

13. The elongate element of claim 11, wherein the elongate element has a substantially solid structure.

14. An elongate element of an apparatus for manipulating an esophagus,
   the elongate element consisting of:
   a distal end;
   a proximal end opposite from the distal end;
   a proximal portion adjacent to the proximal end, the proximal portion being substantially linear or substantially curvilinear; and
   a distal portion adjacent to the distal end, a manipulation section of the distal portion:
      having a substantially two-dimensional configuration defined by at least one deviation extending laterally beyond a first side of a substantially linear path or a substantially curvilinear path of the elongate element and at least another deviation extending laterally beyond a second, opposite side of the substantially linear path or the substantially curvilinear path of the elongate element;
      having a width of greater than 14 mm; and having a rigidity sufficient to move the esophagus and/or flatten the esophagus.

15. The elongate element of claim 14, wherein each of the at least one deviation and the at least another deviation comprises a curved deviation.

* * * * *